United States Patent
Mackool

[11] Patent Number: 6,039,715
[45] Date of Patent: Mar. 21, 2000

[54] ANGULATED PHACOEMULSIFICATION NEEDLE WHOSE OUTER SURFACE CONVERGES AND INNER CHANNEL NARROWS

[76] Inventor: Richard J. Mackool, 31-27 41st St., Astoria, N.Y. 11103

[21] Appl. No.: 09/075,615

[22] Filed: May 11, 1998

[51] Int. Cl.[7] .................................................. A61M 5/32
[52] U.S. Cl. .............................. 604/272; 604/22; 604/27; 606/169
[58] Field of Search ................................. 604/19, 22, 27, 604/272; 606/107, 169

[56] References Cited

U.S. PATENT DOCUMENTS

| | | | |
|---|---|---|---|
| 4,832,683 | 5/1989 | Idemoto et al. ........................... | 604/22 |
| 5,154,694 | 10/1992 | Kelman ..................................... | 604/22 |
| 5,743,871 | 4/1998 | Strukel et al. ............................ | 604/35 |
| 5,830,192 | 11/1998 | Van Voorhis ............................ | 604/280 |

Primary Examiner—Ronald Stright
Assistant Examiner—Michael J. Hayes
Attorney, Agent, or Firm—Cobrin & Gittes

[57] ABSTRACT

A phacoemulsification apparatus includes a needle that is hollow and terminates in an evacuation port and has a straight portion and a bent or angulated portion spaced from the evacuation port. The needle defines an inner channel that narrows from the evacuation port before, at or beyond the angulated portion. The outer surface of the needle is also configured to converge before, at or beyond the bent or angulated portion. A flexible infusion sleeve surrounds the needle longitudinally along the straight portion of the needle and terminates at an area proximal to or in the vicinity of the angulated portion.

15 Claims, 1 Drawing Sheet

ANGULATED PHACOEMULSIFICATION NEEDLE WHOSE OUTER SURFACE CONVERGES AND INNER CHANNEL NARROWS

BACKGROUND OF THE INVENTION

1. Field of the Invention

The invention relates to a phacoemulsification apparatus that is used to control fluid flow transfer within a surgical site of an eye. The apparatus includes a needle whose outer surface converges and inner channel narrows.

2. Discussion of Related Art

A wide array of fluid-irrigated, ultrasonically-operated cutting devices have been developed for ophthalmological surgical techniques such as phacoemulsification—a method for removing a cataract through a surgical incision in the eye.

Heretofore, phacoemulsification involved the use of a dual chambered handpiece consisting of a hollow metallic needle surrounded by a tubular sleeve. The needle is vibrated ultrasonically at selected frequencies and amplitudes to fracture the cataract to be removed and replaced by an intraocular lens. The fractured cataract tissue is aspirated through the needle interior through the use of a suction force. A fluid is infused into the eye through the tubular sleeve to irrigate the eye. The tubular sleeve has been made heretofore preferably of a soft material such as silicone or less desirably of a rigid composition such as metal or teflon.

Phacoemulsification needles come in many different configurations. Some are straight yet their inner channel narrows in diameter in a direction heading away from the open tip and spaced therefrom. Some of these also have an outer surface that converges from the tip, with the inner channel narrowing in diameter for the length of this convergence. Still others are angulated and have an inner channel that is of constant diameter.

U.S. Pat. No. 5,084,009 ('009 patent), entitled FLUID INFUSION SLEEVE FOR USE DURING EYE SURGERY, which issued to Richard Mackool on Jan. 28, 1992, whose contents are incorporated herein by reference, discloses a silicone sleeve and discusses the problems that arise from the incision compressing the non-rigid, pliable silicone sleeve. Such problems include the sleeve collapsing on the vibrating needle so that the needle, which is being vibrated at ultrahigh frequencies, rubs against the sleeve and the irrigation flow path between the needle and the sleeve becoming constricted due to the collapsed sleeve.

The sleeve through which irrigation takes place, i.e., delivering fluid to the eye, should be made of soft material that can deform to match the contour of the eye incision and thereby prevent leakage. To prevent the sleeve from collapsing on the vibrating needle, the '009 patent suggests surrounding the needle with a rigid sleeve that is interposed between the needle and the outer, soft, silicone sleeve. Thus, a collapse of the outer, soft, silicone sleeve will be onto the rigid sleeve rather than in rubbing contact with the vibrating needle.

U.S. Pat. No. 5,505,693 ('693 Patent), entitled "Method and Apparatus For Reducing Friction and Heat Generation By an Ultrasonic Device During Surgery", which issued to Richard Mackool on Apr. 9, 1996 and whose contents are incorporated herein by reference, discloses a soft outer sleeve having a rigid lining, thereby obviating the need for a separate rigid sleeve between the outer sleeve and the needle.

The experience of the applicant, who has performed literally thousands of cataract eye operations, has found that during the course of an eye surgical operation, the tubes that lead to the handpiece of the phacoemulsification instrument from a surgical console are susceptible to unintentional kinking by medical personnel if the tubes are made from soft, pliable material that may elastically expand under pressure. These tubes include the infusion tube from the fluid supply to the handpiece and the discharge tube from the handpiece to the drainage receptacle or suction. There is no vibratory needle within these tubes so there is no risk of making unwanted rubbing contact as would prompt the solution of interposing a rigid sleeve to surround the needle as taught in the '009 patent.

Kinking may lead to severe consequences. If the infusion tube becomes kinked, a pressure loss downstream may lead to deflation of the eye. Such deflation could lead to collapse of certain eye tissues upon each other or upon the surgical instrument which extends into the eye. Either way, the tissues which are most likely to be damaged from such deflation are the cornea, the iris and the lens capsule, all surrounding the cataract. Fragile cells which line the inside of the cornea are known as corneal endothelium and they cannot be regenerated by the eye. Damage to the corneal endothelium can cause permanent damage to the cornea, resulting in a corneal clouding and decreased vision. A corneal transplant may then be necessary.

If the discharge tube becomes inadvertently kinked or, as commonly occurs, blocked by fractured tissue, the eye will still be pressurized, but the surgical operation will cease until the kink or blockage is eliminated. At the time of the kinking or blocking, however, the pressure falls downstream so that upon removal of the kink or blockage, a sudden surge in the outflow rate arises as the downstream vacuum acts to drain the eye due to loss of upstream pressure. This sudden drop in upstream pressure is felt by the eye, tending to create some deflation until normal flow is restored. It would be desirable to avoid such deflation by allowing the infusion tube to expand to hold more fluid and develop elastic energy which upon release can cause increase of flow into the eye and thereby counter the abrupt surge in the outflow upon removal of the kink or blockage. Soft material, such as silicone, elastically expands under pressure build-up and so its use is preferable.

Upon release of the blockage or kinking, the expanded, soft infusion tube contracts back to its unexpanded state and thereby provides a temporarily greater volume of fluid flow per second than was being supplied to the eye before the kinking or blocking arose. Thus, the volumetric loss of fluid during the sudden surge in outflow upon removal of the kink or blockage is better compensated by the larger volume of fluid readily available under pressure in the expanded, soft infusion tube.

U.S. Pat. No. 5,685,841 (the '841 patent) issued to Richard Mackool on Nov. 11, 1997, whose contents are incorporated herein by reference, offers a solution to the kinking problem.

The infusion sleeve may be circular or ellipsoidal in cross-section and is made of a soft, pliable material. Preferably, a rigid, noncompressible sleeve is surrounded by this infusion sleeve and acts as a barrier between the infusion sleeve and the needle in the event the infusion sleeve collapses, thereby preventing undesirable rubbing contact.

The '841 patent reveals a conventional phacoemulsification handpiece arranged to irrigate fluid into the eye and aspirate fluid and tissue from the eye continuously throughout an eye surgery operation. A concentric relationship exists between the needle, the rigid, noncompressible sleeve and the infusion sleeve. The forward end of the infusion sleeve is tapered. There is a vibratory drive in the handpiece for imparting vibratory motion on the hollow needle. The infusion sleeve defines a chamber between its inner wall and the outside of the vibrating hollow needle. Irrigation into the eye is provided normally through this chamber and aspiration from the eye is through the needle.

The irrigation is provided from a gravity fed fluid supply and through an infusion tube to the handpiece. Aspiration is provided through a discharge tube from the handpiece to a drain receptacle. In a known manner, a gate valve is provided to permit flow through the infusion tube to occur. The fluid supply is at a higher elevation than the eye. A pumping mechanism may be present and, when activated, suctions fluid from the eye and through discharge tube.

The tubes may be susceptible to unintentional kinking by medical personnel unless they are made from an incompressible material. If the kinking arises in the discharge tube, the surgical procedure stops but the eye remains inflated under pressure. If the kinking arises in the infusion tube, however, a pressure drop in the eye ensues that leads to its collapse. Such a collapse causes unwanted contact of eye tissue.

It may be desirable to form at least the infusion tube of a soft, elastic, expandable material such as silicone to counteract the momentary flow surge that eventually results if the outflow through the discharge tube becomes blocked, e.g., by tissue fragments. When such blockage arises, pressure decreases downstream to the blockage so that when the blockage is removed, there is a momentary surge in the outflow. Such a sudden event release tends to deflate the eye. To counter this deflation, the infusion tube could be made to expand under a build-up of pressure, as takes place during blockage of the outflow through the discharge tube. When the blockage is removed, the infusion tube would elastically compress back to its unexpanded state and thereby offset the momentary surge in the outflow.

U.S. Pat. No. 5,154,694 to Charles Kelman discloses a tissue scraper device for medical use for which the tip portion of the needle is angulated. Such an angulated needle is currently commercialized by Alcon Laboratories. The angulation on their product is 22°, the outer diameter of the needle varies between 1.1 and 0.9 mm, and the inner diameter between 0.9 and 0.6 mm. The distance between the angulation and the tip is approximately 4 mm. The tip has a distal port with an angulation which varies between 0° (port perpendicular to the axis of the angulated portion of the tip) and 45°.

U.S. Pat. No. 3,589,363 to Banko and Kelman (the '363 patent) discloses a hand held instrument and method for breaking apart and removing by flushing fluid flow undesired material such as tissue from a body site. The instrument contains a vibratory drive connected to a longitudinal shank having an axial bore leading to a mouth at its projecting straight tip, and a conduit leading to an opening at the shank exterior, such that axial vibratory movement of the tip, when pressed axially against the tissue, breaks up the tissue by jack-hammer-like action, for removal by flow of fluid from a source to the site via one of the mouth and opening and its return with broken up tissue via the other of the mouth and opening to a suction source.

This '363 patent teaching covers break up and removal of cataracted eye lens tissue per known surgical procedures. Such procedures are effected through a corneal incision kept as small as possible to minimize patient trauma. In this regard, it is desirable to remove all tissue debris from the posterior capsule.

However, it has been found that in using the straight tip instrument for such purposes, the procedures are burdened by awkwardness in the positioning of the instrument in the surgeon's hand under the extant vibratory conditions, especially when attempting to break up portions of the cataracted lens tissue in remote portions of the posterior chamber in relation to the fixed position of the necessarily small corneal incision. This awkwardness leads to uncomfortable hand and finger positions of the surgeon when holding the vibrating instrument and manipulating it in relation to that fixed location of the corneal incision for bringing the free end of its straight tip into proper "head-on" position for breaking up the lens tissue in the inherently confined spatial areas involved.

While the instrument according to the '363 patent may be provided with a radially extending, sharp pointed projection, this is only used to tear the anterior wall of the capsule covering the lens by back and forth tearing action to obtain access to the lens prior to initiation of the tissue breaking apart procedure. This projection would be of no value in breaking apart the main mass of the lens tissue within its capsule, especially considering that the projection has a pointed end and is positioned with that end remote from the tip mouth through which the flushing fluid flows.

On the other hand, the back and forth jack-hammer-like action of the straight tip of the instrument of the '363 patent, which is used for the actual breaking up of the lens tissue, operates by way of axial or longitudinal direction percussion impulse exerted perpendicularly against the tissue surface as anvil, inherently resulting in a coarse shattering of the tissue.

As a result, the surgeon must take pains to manipulate the tip through many diverse angular positions, while the shank extends through the relatively small incision, to be able to apply the leading transverse face of the longitudinal straight tip in "head-on" relation with the lens tissue, as the very nature of the percussion impulse action is such that the axially vibrating tip makes head-on face-to-face contact with the tissue surface. Also, care must be taken to avoid unduly pressing the tip against the tissue surface of the posterior capsule for fear of puncturing or otherwise damaging unnecessarily that was which is intended to remain intact.

It is desired to configure the needle to enhance cavitational forces near the evacuation port, increase resistance to fluid out flow from the eye, reduce fluid surge, improve infusion capacity, widen tolerances for rigid sleeves and avoid the need for collars on the needle. Such collars are present on some straight needle designs, and act to restrain the rigid sleeve and prevent its forward migration toward the distal end of the needle.

SUMMARY OF THE INVENTION

One aspect of the invention resides in a phacoemulsification needle that is hollow and terminates in an evacuation port and has a bent or angulated portion spaced from the evacuation port. The hollow needle defines an inner channel that narrows from the evacuation port toward, at, or beyond the angulated portion. The outer surface of the needle is likewise configured to converge in a direction from the evacuation port to, at, or beyond the bent or angulated portion.

BRIEF DESCRIPTION OF THE DRAWINGS

For a better understanding of the present invention, reference is made to the following description and accompanying drawings, while the scope of the invention is set forth in the appended claims.

DESCRIPTION OF THE PREFERRED EMBODIMENT

Figure 1:
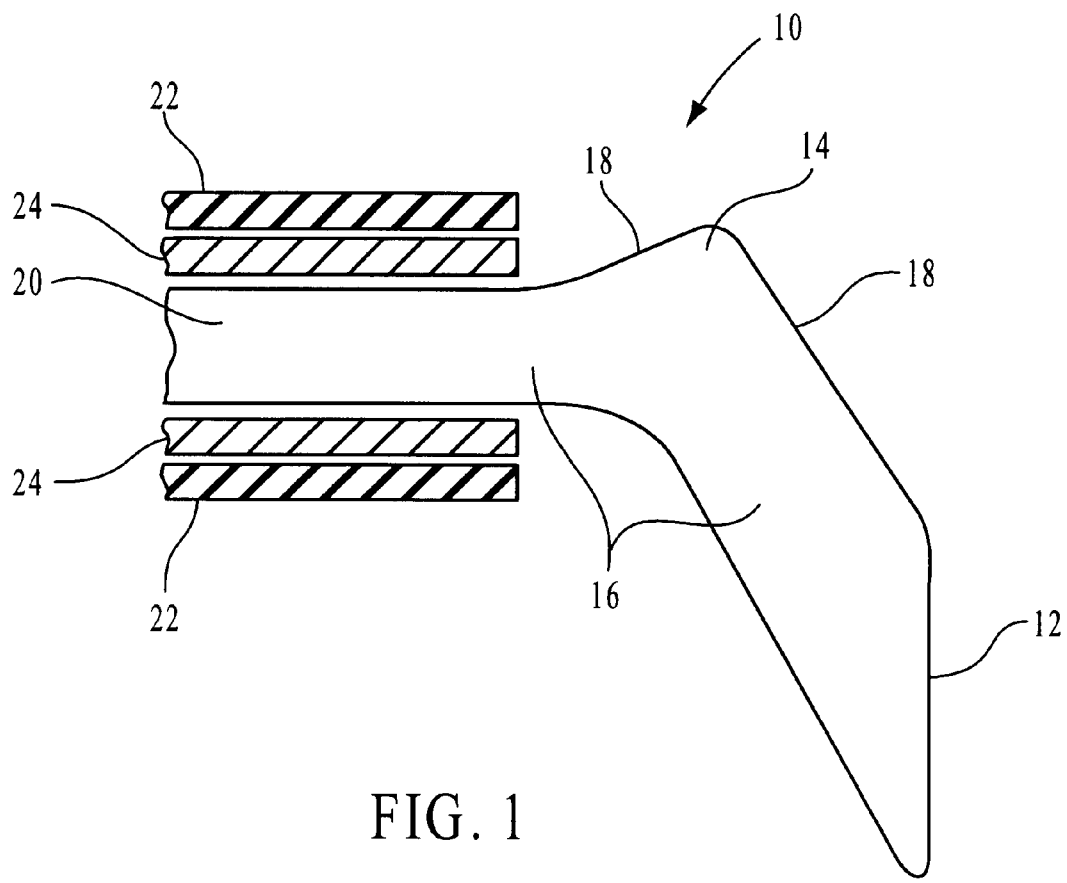
FIG. 1 is a partial elevational plan view of a needle in accordance with the invention.

Turning to the drawings, FIG. 1 shows a phacoemulsification needle 10 that is hollow and terminates in an evacuation port 12 and has a bent or angulated portion 14 spaced from the evacuation port 12. The needle 10 defines a channel 16 that narrows diametrically either between the evacuation port 12 and the angulated portion 14, at the angulated portion 14, or at the remaining portion 20. The outer surface 18 of the needle is likewise configured to narrow diametrically at approximately the same location as does the inner channel 16. Thereafter, the remaining portion 20 of the needle is straight, having inner and outer diameters that remain constant. The needle 10 preferably is metallic.

An infusion sleeve 22, which is flexible, surrounds the straight portion 20. Optionally, a rigid sleeve 24 may be situated between the straight portion 20 and the infusion sleeve 22 to prevent collapse of the infusion sleeve 22 onto the straight portion 20. Such a rigid sleeve may instead be attached to an interior side of the infusion sleeve 22 and thereby serve as a rigid lining.

The point of termination of the flexible infusion sleeve 22 is not important and may vary. The infusion ports of the flexible infusion sleeve 22 should be located proximal to the wider portion of the needle 10, in order to maximize infusion capacity.

With the rigid sleeve 24, the soft infusion sleeve 22 and the needle 10, the construction of each and their relative arrangement and operation may conform to the teaching of the '009 Patent. Without the rigid sleeve 24, the soft infusion sleeve should have a rigid liner in the manner taught by the '693 Patent. In both cases, the needle 10 is preferably angulated in the manner of the present application.

The experience of the applicant, who has performed literally thousands of cataract eye operations, has found that during the course of an eye surgical operation, the phacoemulsification needle 10 of FIG. 1 affords the following advantages:

(1) Greater cavitational forces or power over that for straight configured needles are created because of a poor hydrodynamic surface of the angulated tip. In essence, this means that the more blunt a vibrating object is, the greater the pressure changes are which develop in front of the object as it moves forward and backward very rapidly in fluid. It is extremely difficult to measure this increase in cavitational force (as compared to a straight needle), but it is probably on the order of 10 times greater based upon the clinical experience of the applicant in several thousand operations with both standard (straight) and angulated needle designs.

The increased level of power is a result of: (a) the greater cavitation at the tip; and (b) the fact that the posterior surface of the needle near its tip also creates cavitation as it moves backward, therefore creating cavitational and mechanical forces both in front of and behind the needle as it moves back and forth within tissue.

(2) Increased resistance to fluid out flow from the eye helps limit the outflow rate with vacuum-based aspiration sources, which create fluid flow by creating a constant vacuum level. The resistance to flow is proportional to the area of the cross sectional portion of the needle at any location. Therefore, if the diameter is reduced to half, the area is reduced to 25% of the original area (area is equal to 3.14 multiplied by the square of the radius). This reduction in area would result in reduced flow rate through the area and this reduction in flow rate would be most significant at the higher level of flow rates generally seen at the time of a fluid surge. Therefore, the higher vacuum levels which are developed just prior to fluid surge would in effect be mitigated by the constricted region.

(3) Reduced fluid surge at the time of release of an obstruction from the aspiration line with all types of aspiration pumps, such as Venturi, peristaltic or others.

(4) Improved infusion capacity due to availability of added space for fluid infusion into the eye between the needle and the surrounding infusion sleeve(s). This added space is found between the outer surface of the needle and the inner surface of the outer infusion sleeve. The greater the area available for infusion fluid to pass around the needle, the greater the infusion capacity. This would have its limits i.e., as soon as a dimension of this area approaches in size a dimension of the area equal to the narrowest portion of the infusion line 27 at any point, the maximum infusion capacity would have been attained. Practically speaking, the "bottleneck" in current systems used in eye surgery is always in the region between the needle and the sleeve(s).

(5) Widens tolerances for rigid sleeves, which makes it easier to design and manufacture these sleeve/tip combinations. The wider tolerances come from the added spacing or gap 29 created between the outer surface of the needle and the inner surface of the outer infusion sleeve. Preferably, the area between the inner surface of the outer infusion sleeve and the outer surface of the needle should at least equal the spacing (area) of the infusion tubing which is most narrow (has the smallest total area).

(6) Avoids the need for a collar on the needle in order to restrain the rigid sleeve, because the rigid sleeve is restrained from forward migration by the wider, fuller portion of the needle. The converging outer surface of the needle acts to prevent the rigid sleeve from slipping forward over the angulated portion of the needle, and into the eye. Therefore, no other means are necessary (such as screwing of the sleeve or placing a restrictive, elevated area on the surface of the needle) in order to prevent this very undesirable event from occurring.

However, the infusion sleeve only extends to the point of angulation, and the wider diameter of the needle beyond the angulation (i.e., toward the tip of the needle) thus has no affect on infusion capacity. For purposes of discussion, if the outer diameter of the needle is decreased from 1.0 mm to 0.6 mm, the area occupied within the sleeve by the needle is reduced by nearly two-thirds. Thus a smaller diameter rigid sleeve could be used and the area between the outer facing surface of the rigid sleeve and the inner facing surface of the outer sleeve would increase. This area is the "bottleneck" region, which by increasing its areal dimension, significantly increases infusion capacity.

Figure 2:
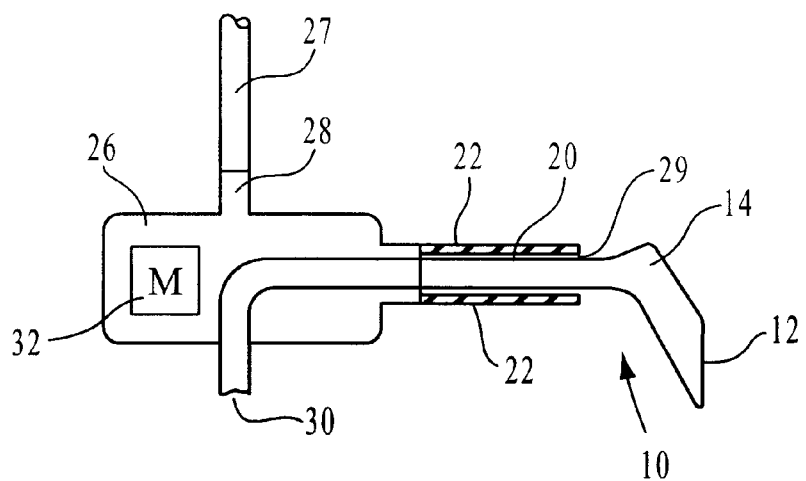
FIG. 2 is a schematic representation of the needle of FIG. 1 extending from a phacoemulsification instrument.

FIG. 2 shows schematically the needle of FIG. 1 in position, held by flanges of a phacoemulsification handpiece 26. For the sake of brevity, the details of the structure of the phacoemulsification handpiece 26 is omitted because such is conventional. That is, it has an infusion entry port 28, an evacuation discharge port 30 and a motor 32 to impart vibratory motion on the needle 10.

While the foregoing description and drawings represent the preferred embodiments of the present invention, it will be understood that various changes and modifications may be made without departing from the spirit and scope of the present invention.

What is claimed is:

1. A phacoemulsification apparatus comprising:

an elongated, hollow needle body having an evacuation port, a straight portion, and an angulated portion between said evacuation port and said straight portion, said angulated portion changing an angular orientation of said body with respect to said straight portion, said body having an elongated channel that defines said hollow of said body, said body defining said elongated channel to narrow diametrically as the elongated channel extends in a direction toward said straight portion before, at or beyond said angulated portion, said body having an elongated exterior configured to narrow diametrically as the elongated exterior extends in a direction toward said straight portion before, at, or beyond said angulated portion, both said elongated channel and said elongated exterior narrowing in diameter in a direction away from said evacuation port between said straight portion and said angulated portion.

2. An apparatus as in claim 1, further comprising an infusion sleeve that is flexible, said sleeve having a free end in alignment with said angulated portion such that said angulated portion is arranged outside confines of said sleeve and beyond the free end of said sleeve.

3. An apparatus as in claim 2, further comprising a rigid sleeve arranged between the infusion sleeve and the straight portion.

4. An apparatus as in claim 3, further comprising a phacoemulsification handpiece securing said infusion sleeve and said body in position relative to each other, said handpiece having a driver that imparts vibratory motion to the body.

5. An apparatus as in claim 2, further comprising a phacoemulsification handpiece securing said infusion sleeve and said body in position relative to each other, said handpiece having a driver that imparts vibratory motion to the body.

6. An apparatus as in claim 5, further comprising a handpiece securing said infusion sleeve and said body in position relative to each other, said handpiece having a driver that imparts vibratory motion to the body; an infusion line connected to the phacoemulsification handpiece and in fluid communication with a gap between said infusion sleeve and said elongated, hollow needle body, said infusion line being tubular with a hollow region having a dimension defined by an area that is at least the same size as a dimension defined by an area of the gap.

7. An apparatus as in claim 2, further comprising a rigid lining spaced interiorly of said infusion sleeve.

8. A phacoemulsification apparatus comprising:

an elongated, hollow needle body having an evacuation port, a straight portion, and an angulated portion between said evacuation port and said straight portion, said angulated portion changing an angular orientation of said body with respect to said straight portion, said body having an elongated channel that defines said hollow of said body, said body defining said elongated channel to narrow diametrically as the elongated channel extends in a direction toward said straight portion before, at or beyond said angulated portion, said body having an elongated exterior configured to narrow diametrically as the elongated exterior extends in a direction toward said straight portion before, at, or beyond said angulated portion;

an infusion sleeve that is flexible, said sleeve having a free end in alignment with said angulated portion such that said angulated portion is arranged outside confines of said sleeve and beyond the free end of said sleeve;

a phacoemulsification handpiece securing said infusion sleeve and said body in position relative to each other, said handpiece having a driver that imparts vibratory motion to the body; and an infusion line connected to the phacoemulsification handpiece and in fluid communication with a gap between said infusion sleeve and said elongated, hollow needle body, said infusion line being tubular with a hollow region having a dimension defined by an area that is at least the same size as a dimension defined by an area of the gap.

9. A phacoemulsification apparatus, comprising:

an elongated, hollow needle body having an evacuation port, a straight portion, and an angulated portion between said evacuation port and said straight portion, said angulated portion changing an angular orientation of said body with respect to said straight portion, said body having an elongated channel that defines said hollow of said body and having an elongated outer surface, both said elongated channel and said elongated outer surface having respective portions between said straight portion and said evacuation port that narrow diametrically in a direction away from said evacuation port.

10. An apparatus as in claim 9, further comprising an infusion sleeve that is flexible, said sleeve having a free end in alignment with said angulated portion such that said angulated portion is arranged outside confines of said sleeve and beyond the free end of said sleeve.

11. An apparatus as in claim 10, further comprising a rigid sleeve arranged between the infusion sleeve and the straight portion.

12. An apparatus as in claim 11, further comprising a phacoemulsification handpiece securing said infusion sleeve and said body in position relative to each other, said handpiece having a driver that imparts vibratory motion to the body.

13. An apparatus as in claim 10, further comprising a phacoemulsification handpiece securing said infusion sleeve and said body in position relative to each other, said handpiece having a driver that imparts vibratory motion to the body.

14. An apparatus as in claim 13, further comprising an infusion line connected to the phacoemulsification handpiece and in fluid communication with a gap between said infusion sleeve and said elongated, hollow needle body, said infusion line being tubular with a hollow region having a dimension defined by an area that is at least the same size as a dimension defined by an area of the gap.

15. An apparatus as in claim 10, further comprising a rigid lining spaced interiorly of said infusion sleeve.

* * * * *

UNITED STATES PATENT AND TRADEMARK OFFICE
CERTIFICATE OF CORRECTION

PATENT NO. : 6,039,715
DATED : March 21, 2000
INVENTOR(S) : Richard J. Mackool

It is certified that error appears in the above-indentified patent and that said Letters Patent is hereby corrected as shown below:

Claims 6, 8 and 14, third line from the bottom, after "region" insert --, the gap-- last line change "gap" to -- hollow region --

Signed and Sealed this

Twenty-seventh Day of March, 2001

Attest:

NICHOLAS P. GODICI

*Attesting Officer*   *Acting Director of the United States Patent and Trademark Office*